(12) United States Patent
Chiang et al.

(10) Patent No.: US 8,557,603 B2
(45) Date of Patent: Oct. 15, 2013

(54) SYNTHETIC PEPTIDES, METHODS AND KITS FOR DIAGNOSING AUTOIMMUNE DISEASES

(75) Inventors: Bor-Luen Chiang, Taipei (TW); Yao-Hsu Yang, Taipei (TW); Chung-Sheng Huang, Toorak (AU)

(73) Assignee: FlySun Development Co. Ltd., Taipei (TW)

( * ) Notice: Subject to any disclaimer, the term of this patent is extended or adjusted under 35 U.S.C. 154(b) by 213 days.

(21) Appl. No.: 13/143,088

(22) PCT Filed: Jan. 2, 2009

(86) PCT No.: PCT/AU2009/000006
§ 371 (c)(1),
(2), (4) Date: Jul. 1, 2011

(87) PCT Pub. No.: WO2010/075604
PCT Pub. Date: Jul. 8, 2010

(65) Prior Publication Data
US 2011/0287456 A1    Nov. 24, 2011

(51) Int. Cl.
G01N 33/564 (2006.01)
G01N 33/68 (2006.01)
G01N 33/53 (2006.01)
C07K 14/435 (2006.01)

(52) U.S. Cl.
USPC ............ 436/506; 436/513; 435/7.1; 530/324; 422/430

(58) Field of Classification Search
None
See application file for complete search history.

(56) References Cited

U.S. PATENT DOCUMENTS

| | | | | |
|---|---|---|---|---|
| 5,998,223 A | * | 12/1999 | Matsuura et al. | 436/518 |
| 6,858,210 B1 | * | 2/2005 | Marquis et al. | 424/185.1 |
| 7,745,146 B2 | * | 6/2010 | Iverson et al. | 436/518 |
| 2007/0060743 A1 | | 3/2007 | Tang et al. | |

FOREIGN PATENT DOCUMENTS

| | | |
|---|---|---|
| WO | WO2006/109312 A2 * | 10/2006 |
| WO | WO 2010/075604 A1 | 7/2010 |

OTHER PUBLICATIONS

Yang et al. "Identification and characterization of IgA antibodies against beta2-glycoprotein I in childhood Henoch-Schönlein purpura" Br J Dermatol Oct. 2012;167(4):874-81.*

Kawakami, T. et al."High titer of Serum Antiphospholipid Antibody Levels in Adult Henoch-Schonlein Purpura and Cutaneous Leukocytoclastic Angiitis", Arthritis & Rheumatism, Arthritis Care & Research (2008), 59(4), 561-567.

\* cited by examiner

*Primary Examiner* — Christine Foster
(74) *Attorney, Agent, or Firm* — Chih Feng Yeh; Huntington IP Consulting Co., Ltd.

(57) ABSTRACT

Provided herein are synthetic peptides, methods and kits for easy detecting or diagnosing an autoimmune disease, particularly, Henoch-Schönlein purpura (HSP), based on the detection of autoimmune antibodies with peptides derived from β-2-glycoprotein-1 (β2-GPI).

7 Claims, 11 Drawing Sheets

(A)

(B)

(C)

(D)

(E)

(F)

(G)

(H)

SEQUENCE LISTING

<160> NUMBER OF SEQ ID NOS: 15

<210> SEQ ID NO 1
<211> LENGTH: 28
<212> TYPE: PRT
<213> ORGANISM: Homo sapiens

<400> SEQUENCE: 1

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp
            20                  25

<210> SEQ ID NO 2
<211> LENGTH: 32
<212> TYPE: PRT
<213> ORGANISM: Homo sapiens

<400> SEQUENCE: 2

Arg Thr Cys Pro Lys Pro Asp Asp Leu Pro Phe Ser Thr Val Val Pro
1               5                   10                  15

Leu Lys Thr Phe Tyr Glu Pro Gly Glu Glu Ile Thr Tyr Ser Cys Lys
            20                  25                  30

<210> SEQ ID NO 3
<211> LENGTH: 27
<212> TYPE: PRT
<213> ORGANISM: Homo sapiens

<400> SEQUENCE: 3

Lys Pro Gly Tyr Val Ser Arg Gly Gly Met Arg Lys Phe Ile Cys Pro
1               5                   10                  15

Leu Thr Gly Leu Trp Pro Ile Asn Thr Leu Lys
            20                  25

<210> SEQ ID NO 4
<211> LENGTH: 19
<212> TYPE: PRT
<213> ORGANISM: Homo sapiens

<400> SEQUENCE: 4

Lys Cys Thr Pro Arg Val Cys Pro Phe Ala Gly Ile Leu Glu Asn Gly
1               5                   10                  15

Ala Val Arg

<210> SEQ ID NO 5
<211> LENGTH: 28
<212> TYPE: PRT
<213> ORGANISM: Homo sapiens

<400> SEQUENCE: 5

Arg Tyr Thr Thr Phe Glu Tyr Pro Asn Thr Ile Ser Phe Ser Cys Asn
1               5                   10                  15

Thr Gly Phe Tyr Leu Asn Gly Ala Asp Ser Ala Lys
            20                  25

<210> SEQ ID NO 6
<211> LENGTH: 20
<212> TYPE: PRT
<213> ORGANISM: Homo sapiens

-continued

```
<400> SEQUENCE: 6

Asp Ser Ala Lys Cys Thr Glu Glu Gly Lys Trp Ser Pro Glu Leu Pro
1               5                   10                  15

Val Cys Ala Pro
            20

<210> SEQ ID NO 7
<211> LENGTH: 29
<212> TYPE: PRT
<213> ORGANISM: Homo sapiens

<400> SEQUENCE: 7

Lys Trp Ser Pro Glu Leu Pro Val Cys Ala Pro Ile Ile Cys Pro Pro
1               5                   10                  15

Pro Ser Ile Pro Thr Phe Ala Thr Leu Arg Val Tyr Lys
            20                  25

<210> SEQ ID NO 8
<211> LENGTH: 31
<212> TYPE: PRT
<213> ORGANISM: Homo sapiens

<400> SEQUENCE: 8

Arg Val Tyr Lys Pro Ser Ala Gly Asn Asn Ser Leu Tyr Arg Asp Thr
1               5                   10                  15

Ala Val Phe Glu Cys Leu Pro Gln His Ala Met Phe Gly Asn Asp
            20                  25                  30

<210> SEQ ID NO 9
<211> LENGTH: 29
<212> TYPE: PRT
<213> ORGANISM: Homo sapiens

<400> SEQUENCE: 9

Asp Thr Ile Thr Cys Thr Thr His Gly Asn Trp Thr Lys Leu Pro Glu
1               5                   10                  15

Cys Arg Glu Val Lys Cys Pro Phe Pro Ser Arg Pro Asp
            20                  25

<210> SEQ ID NO 10
<211> LENGTH: 19
<212> TYPE: PRT
<213> ORGANISM: Homo sapiens

<400> SEQUENCE: 10

Arg Pro Asp Asn Gly Phe Val Asn Tyr Pro Ala Lys Pro Thr Leu Tyr
1               5                   10                  15

Tyr Lys Asp

<210> SEQ ID NO 11
<211> LENGTH: 57
<212> TYPE: PRT
<213> ORGANISM: Homo sapiens

<400> SEQUENCE: 11

Lys Ala Thr Phe Gly Cys His Asp Gly Tyr Ser Leu Asp Gly Pro Glu
1               5                   10                  15

Glu Ile Glu Cys Thr Lys Leu Gly Asn Trp Ser Ala Met Pro Ser Cys
            20                  25                  30
```

```
Lys Ala Ser Cys Lys Val Pro Val Lys Ala Thr Val Val Tyr Gln
        35                  40                  45

Gly Glu Arg Val Lys Ile Gln Glu Lys
    50                  55

<210> SEQ ID NO 12
<211> LENGTH: 20
<212> TYPE: PRT
<213> ORGANISM: Homo sapiens

<400> SEQUENCE: 12

Phe Lys Asn Gly Met Leu His Gly Asp Lys Val Ser Phe Phe Cys Lys
1               5                   10                  15

Asn Lys Glu Lys
            20

<210> SEQ ID NO 13
<211> LENGTH: 18
<212> TYPE: PRT
<213> ORGANISM: Homo sapiens

<400> SEQUENCE: 13

Lys Glu Lys Lys Cys Ser Tyr Thr Glu Asp Ala Gln Cys Ile Asp Gly
1               5                   10                  15

Thr Ile

<210> SEQ ID NO 14
<211> LENGTH: 20
<212> TYPE: PRT
<213> ORGANISM: Homo sapiens

<400> SEQUENCE: 14

Asp Gly Thr Ile Glu Val Pro Lys Cys Phe Lys Glu His Ser Ser Leu
1               5                   10                  15

Ala Phe Trp Lys
            20

<210> SEQ ID NO 15
<211> LENGTH: 19
<212> TYPE: PRT
<213> ORGANISM: Homo sapiens

<400> SEQUENCE: 15

Lys Glu His Ser Ser Leu Ala Phe Trp Lys Thr Asp Ala Ser Asp Val
1               5                   10                  15

Lys Pro Cys
```

SYNTHETIC PEPTIDES, METHODS AND KITS FOR DIAGNOSING AUTOIMMUNE DISEASES

CROSS-REFERENCE TO RELATED APPLICATION

This application claim priority to PCT International Application No. PCT/AU2009/000006, filed Jan. 2, 2009, the entireties of which is incorporated herein by reference.

FIELD OF THE INVENTION

The present invention relates to synthetic peptides, methods and kits for detecting or diagnosing autoimmune diseases. More particularly, the present invention provides synthetic peptides, methods and kits for easy detection or diagnosis of Henoch-Schönlein purpura (HSP) based on the detection of autoimmune antibodies with synthetic peptides derived from β-2-glycoprotein-1 (β2-GPI).

BACKGROUND OF THE INVENTION

Purpura results from the extravasation of blood from the vasculature into the skin or mucous membranes. Depending on their size, purpuric lesions are traditionally classified as petechiae (pinpoint hemorrhages less than 2 mm in greatest diameter), purpura (2 mm to 1 cm) or ecchymoses (more than 1 cm). Although purpura itself is not dangerous, it may be the sign of an underlying life-threatening disorder. Therefore, investigation to confirm a diagnosis or to seek reassurance is important.

Henoch-Schönlein purpura (HSP) is a disease of systemic vasculities, inflammation of blood vessels, characterized by deposition of IgA in the skin or kidney. The hallmarks are nonthrombocytopenic purpura, abdominal pain, arthritis and nephritis. HSP is the most common form of vasculities in children. HSP can occur any time in life, but it usually happens in children between 2 to 11 years of age, with a prevalent rate twice in male as that in females. To date, no single test for HSP exists and the doctor may need to perform a series of careful history and physical examination, and a few key laboratory tests to confirm a diagnosis of HSP. Indicated tests include a complete blood cell count with platelet count, a peripheral blood smear, and prothrombin and activated partial thromboplastin times, a check for hematuria in urine sample, and the skin or/and kidney biopsy samples.

Therefore, there exists in this art an improved way of early diagnosing, detecting or confirming the condition of a patient having or suspected of having HSP, and thereby facilitating in providing early treatments to patients in need thereof.

SUMMARY

The present invention relates to the use of synthetic peptides derived from antigenic determinatants of a protein, β-2-glycoprotein-1 (β2-GPI), recognized by autoantibodies of patients who suffer from Henoch-Schönlein purpura (HSP), such peptides may react with autoimmune antibodies of a patient suffering from Henoch-Schönlein purpura.

Accordingly, in one aspect, this invention provides a synthetic peptide for the easy detection or diagnosis of autoantibodies in a subject having or suspected of having HSP. The synthetic peptide is derived from β2-GPI and comprises an amino acid sequence at least 80% identical with a sequence selected from the group consisting of SEQ ID NO: 3, SEQ ID NO: 5, SEQ ID NO: 7, SEQ ID NO: 11 and SEQ ID NO: 12.

Surprisingly, the peptide synthesized according to this invention proved to be suitable for the specific diagnosis of HSP.

Accordingly, in another aspect, this invention provides a method for detecting or diagnosing a subject having or suspected of having Henoch-Schönlein purpura, comprising the steps of: obtaining a biological sample from the subject; and detecting an autoantibody in the biological sample by mixing the biological sample with the synthetic peptide prepared in accordance with the procedure described in one preferred example of this invention, so as to react the autoantibody with the synthetic peptide and thereby forming a complex in an immunologicial reaction. Preferably, the synthetic peptide is derived from β2-GPI and comprises an amino acid sequence at least 80% identical to a sequence selected from the group consisting of SEQ ID NO: 3, SEQ ID NO: 5, SEQ ID NO: 7, SEQ ID NO: 11 and SEQ ID NO: 12. In one embodiment, the immunologicial reaction is an enzyme-linked immunosorbent assay (ELISA). In one preferred embodiment, the autoantibody forms a complex with the synthetic peptide derived from β2-GPI, which comprises an amino acid sequence at least 90% identical to SEQ ID NO: 3. The autoantibody comprises an immunoglobulin A (IgA). In one embodiment, the biological sample is selected from the group consisting of a skin biopsy sample, a whole blood sample, a serum sample, a plasma sample, a urine sample, a mucus sample and purified or filtered forms thereof.

In a further aspect, the present invention provides a kit for detecting or diagnosing a subject having or suspected of having HSP. The kit comprises a container, reagents for detecting an autoantibody in a biological sample, wherein the reagents comprise at least one β2-GPI-derived peptide synthesized in accordance with the procedure described in one example of this invention, the peptide comprises an amino acid sequence at least 80% identical to a sequence selected from the group consisting of SEQ ID NO: 3, SEQ ID NO: 5, SEQ ID NO: 7, SEQ ID NO: 11 and SEQ ID NO: 12; and a legend associated with the container and indicates how to use the β2-GPI-derived peptides for detecting the autoantibody in the biological sample. In one embodiment, the kit further comprises a negative control that indicates the normal level of the autoantibody forms a complex with the β2-GPI-derived peptide having an amino acid sequence at least 80% identical to any of SEQ ID NOs: 3, 5, 7, 11 and 12 in a healthy subject. The biological sample is selected from the group consisting of a skin biopsy sample, a whole blood sample, a serum sample, a plasma sample, a urine sample, a mucus sample and purified or filtered forms thereof.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE INVENTION

Figure 1:
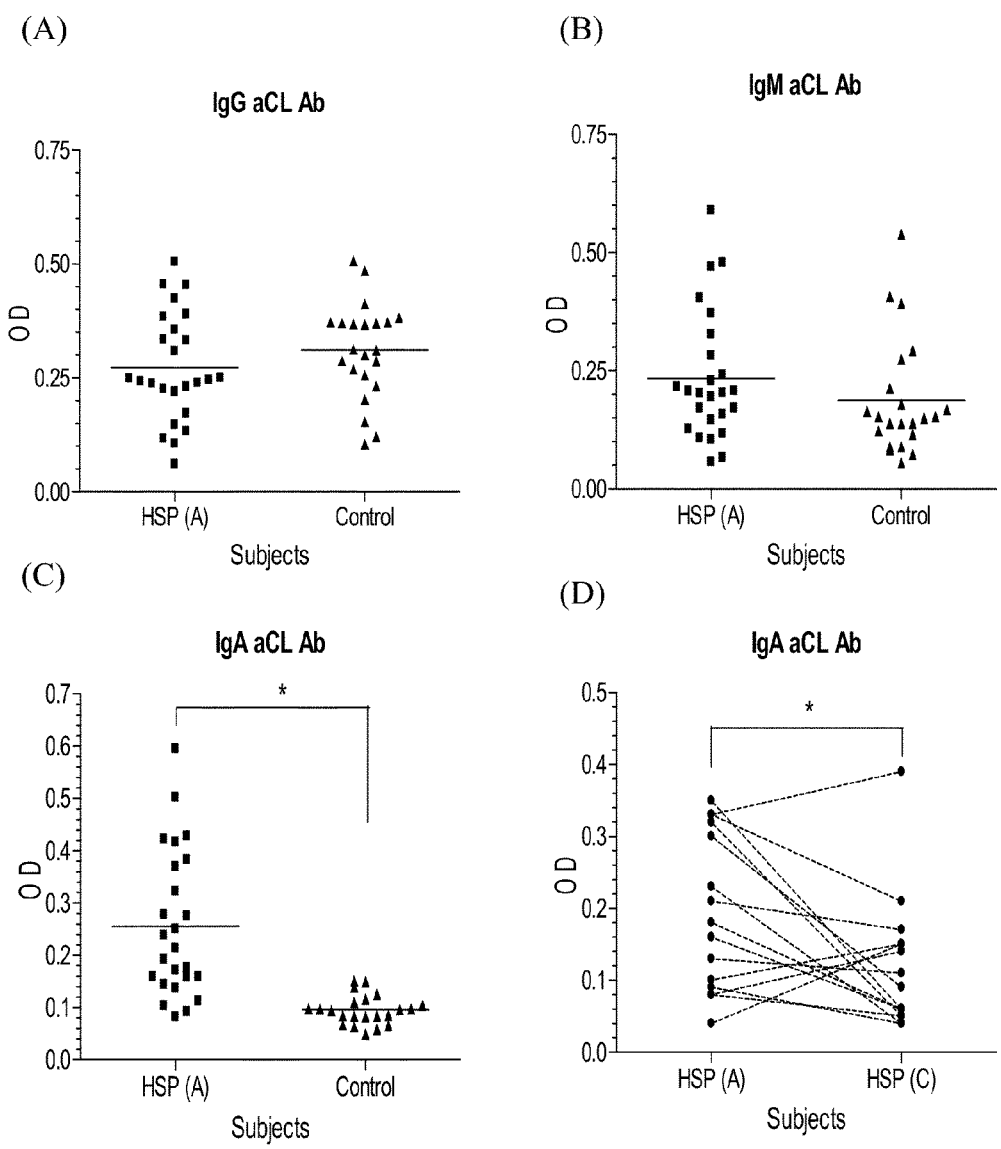
FIG. 1A to 1C illustrate the plasma levels of (A) IgG, (B) IgM, (C) IgA against anticardiolipin (aCL) (presented as OD) measured in children with acute HSP in accordance with one embodiment of this invention, a mean value in each group is represented by a lateral line in each panel.
FIG. 1D is a comparison of IgA aCL antibody level between patients with acute HSP (A) and HSP patients whom are in convalescent phase (C), dashed lines illustrate the data points that are in comparison, with * indicates those that are statistically significant.

The embodiments described and the terminology used herein are for the purpose of describing exemplary embodiments only, and are not intended to be limiting. The scope of the present invention is intended to encompass additional embodiments not specifically described herein, but that would be apparent to one skilled in the art upon reading the present disclosure and practicing the invention.

β2-GPI-Derived Peptides as Markers for the Occurrence of Henoch-Schönlein Purpura (HSP)

The present invention provides specific markers or peptides derived from an autoantigen as indicatives of the occurrence of HSP. Such peptides are useful in the detection, diagnosis or confirmation of HSP.

Experiments conducted during the development of the present invention resulted in the identification of an autoantigen, particularly, a plasma protein, β-2-glycoprotein-1 (β2-GPI), which was isolated from subjects such as human suffering from HSP. Accordingly, β2-GPI-derived peptides recognized by HSP specific autoimmune antibodies are developed as a tool that allows a physician to accurately diagnosis and confirm a clinical HSP condition and subsequently provide treatment to patients in need thereof.

In some embodiments, the present invention provides synthetic peptides, methods and kits for detecting or diagnosing HSP based on detection of autoantibodies with synthetic peptides derived from beta-2-glycoprotein-1.

As used herein, the term "subject" refers to any animal (e.g., a mammal), including, but are not limited to humans, non-human primates, which is to be subjected under the diagnosis of this invention. Typically, the term "patient" and "subject" are used interchangeably herein in reference to a human subject.

As used herein, the term "subject having or suspected of having HSP" refers to a subject that presents one or more symptoms indicative of HSP or is being screened for HSP. A subject suspected of having HSP may also have one or more other risk factors, and is generally not been tested for HSP. A "subject suspected of having HSP" also encompasses an individual who has received an initial diagnosis but for whom the severity of HSP is not known. The term further includes people who once had HSP but whose symptoms have ameliorated.

Beta-2-glycoprotein-1 is one of several human plasma proteins that have been highly purified, crystallized, and characterized, it consists of a polypeptide containing 345 amino acid residues with a molecular weight around 50 kDa. It is conventionally known to act as an anticoagulant in endogenous coagulation system and is an absolute requirement for the binding of "antiphospholipid (aPL)" antibodies purified from patients with autoimmune disease when assayed using anionic phospholipid ELISAs. β2-GP1 also binds to low density lipoprotein (LDL) and has been suggested to be a useful marker for the detection of cardiovascular disease in saliva immunoassay (see U.S. Pat. No. 5,900,356 and US 2003/0100036 A1).

In accordance with one embodiment of this study, the full length of β2-GP1 polypeptide is randomly divided into 15 fragments, with or without overlapping amino acid residues in each fragment. Each peptide fragment contains about 18 to 57 amino acid residues of human β2-GP1. The β2-GP1-derived peptide may be synthesized in accordance with any standard peptide synthesis protocol in the art. In one embodiment, the β2GP1-derived peptides were synthesized by use of a solid-phase peptide synthesizer (ABI433A peptide synthesizer, Applied Biosystems Inc., Life Technologies Corp., Foster City, Calif., USA) in accordance with the manufacturer's protocols. The synthetic peptides were designated as P-1 (SEQ ID NO: 1), P-2 (SEQ ID NO: 2), P-3 (SEQ ID NO: 3), P-4 (SEQ ID NO: 4), P-5 (SEQ ID NO: 5), P-6 (SEQ ID NO: 6), P-7 (SEQ ID NO: 7), P-8 (SEQ ID NO: 8), P-9 (SEQ ID NO: 9), P-10 (SEQ ID NO: 10), P-11 (SEQ ID NO: 11), P-12 (SEQ ID NO: 12), P-13 (SEQ ID NO: 13), P-14 (SEQ ID NO: 14), and P-15 (SEQ ID NO: 15); and are described in detail in Table 1 in one preferred example.

Any skilled person in this art may modify the synthesized peptides by methods (such as a computer simulation program) that predict the effect on polypeptide conformation of a change in polypeptide sequence, and thus may "design" or "modify" a β2-GP1-derived peptide based on the information disclosed herein by proposing and testing a modified β2-GP1-derived peptide to determine whether the modified β2-GP1-derived peptide retains a desired function or conformation. The β2-GP1-derived peptide may be modified specifically to alter a feature of the peptide unrelated to its physiological activity. For example, cystein residues can be substituted or deleted to prevent unwanted disulfide linkage. Similarly, certain amino acids can be changed and/or deleted without affecting the physiological activity of the peptide in this study (i.e., its ability to bind to a HSP specific autoantibody in an immunoassay). This invention thus encompasses functionally equivalent derivatives of β2-GP1-derived peptides synthesized in one embodiment of this invention, including peptides having conservative amino acid substitutions. Conservative substitutions of amino acids include substitutions made amongst amino acids within the following groups: (a) M, I, L, V; (b) F, Y, W; (c) K, R, H; (d): A, G; (e) S, T; (f) Q, N; (g) E, D; and (h) C, M.

Detection of Autoantibodies with β2-GP1-Derived Peptides

The synthetic β2-GP1 peptides were used as a tool for detecting or binding to HSP specific autoantibodies in a subject. Accordingly, this invention provides a method for detecting or diagnosing a subject having or suspected of having Henoch-Schönlein purpura, comprising the steps of: obtaining a biological sample from the subject; and detecting an autoantibody in the biological sample by mixing the biological sample with the synthetic β2GP1 peptide prepared as described above, so as to react the autoantibody with the synthetic β2GP1 peptide and thereby forming a complex in an immunological reaction. Preferably, the synthetic β2GP1 peptide comprises an amino acid sequence at least 80% identical to a sequence selected from the group consisting of SEQ ID NO: 3, SEQ ID NO: 5, SEQ ID NO: 7, SEQ ID NO: 11 and SEQ ID NO: 12. More preferably, the synthetic β2-GP1 peptide comprises an amino acid sequence at least 81%, 82%, 83%, 84%, 85%, 86%, 87%, 88%, 89%, 90%, 91%, 92%, 93%, 94%, 95%, 96%, 97%, 98%, 99% or 100% identical to a sequence selected from the group consisting of SEQ ID NO: 3, SEQ ID NO: 5, SEQ ID NO: 7, SEQ ID NO: 11 and SEQ ID NO: 12. In a most preferred example, the synthesized β2-GP1 peptide comprises an amino acid sequence at least 90% identical to SEQ ID NO: 3. Percentage of identity is a measure of the number of identical amino acid residues in an uninterrupted linear sequence of a polypeptide when compared to a target polypeptide sequence of specified length. As used herein, "identity" of a sequence means that the compared amino acid residues in two separate sequences are identical. Thus, 100% identity means, for example, that upon comparing 20 sequential amino acid residues in two different molecules, both 20 residues in the two different molecules are identical. The biological sample described herein includes, but is not limited to, a skin biopsy sample, a whole blood sample, a serum sample, a plasma sample, a urine sample, a mucus sample and purified or filtered forms thereof.

Antibody binding may be detected by techniques known in the art, such as radioimmunoassay, enzyme-linked immunosorbent assay (ELISA), "sandwich" immunoassay, in situ immunoassays (e.g., using colloidal gold, enzyme or radioisotope labels), western blot, agglutination assay (e.g., gel agglutination assay, hemagglutination assay and etc), complement fixation assay, immunofluorescence assay, and immunoelectrophoresis assay and etc. In one embodiment, antibody binding is detected by use of ELISA. In one embodiment, the autoantibody comprises an immunoglobulin A (IgA). In some embodiments, autoantibodies are detected in bodily fluids, including but are not limited to whole blood, serum, plasma, mucus, urine and purified or filtered forms thereof. In one preferred example, autoantibodies were detected from a plasma sample. In other embodiments, autoantibodies are detected from a skin biopsy sample that reveals white blood cells in the skin and deposits of IgA.

To provide those skilled in the art tools to use the present invention, the synthetic β2-GP1 peptides of the invention are assembled into kits for the diagnosis, detection or confirmation of HSP. In preferred embodiments, the presence of autoantibodies reactive to the synthetic β2-GP1 peptides of this invention is used to provide prognosis to a subject. For example, the detection of high level of autoantibodies reactive to the β2-GP1-derived peptides, as compared to controls, in a sample is indicative of occurrence of HSP. The information provided is also used to direct the course of treatment. For example, if a subject is found to have autoantibodies against peptides derived from an autoantigen, (i.e., β2-GP1), therapies for the treatment of HSP may be started at an earlier time when they are more likely to be effective.

In one embodiment, the present invention provides a kit for HSP diagnosis by use of at least one β2-GPI-derived peptides. The components included in the kits are: a container, reagents for detecting an autoantibody in a biological sample, wherein the reagents comprise at least one synthetic β2-GPI peptide synthesized in accordance with the procedure described in one example of this invention, the peptide comprises an amino acid sequence at least 80% identical to a sequence selected from the group consisting of SEQ ID NO: 3, SEQ ID NO: 5, SEQ ID NO: 7, SEQ ID NO: 11 and SEQ ID NO: 12; and a legend associated with the container and indicating how to use the synthetic β2-GPI peptides for detecting the autoantibody in the biological sample. The legend may be in a form of pamphlet, tape, CD, VCD or DVD. The kit may further comprise a negative control that indicates the normal level of the autoantibody that forms a complex with the synthetic β2-GPI peptide having an amino acid sequence at least 80% identical to any of SEQ ID NO: 3, 5, 7, 11 and 12 in a healthy subject.

Unless defined otherwise, all technical and scientific terms used herein have the same meaning as commonly understood by one of the ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods and examples are illustrative only and not limiting.

The singular forms "a", "and", and "the" are used herein to include plural referents unless the context clearly dictates otherwise. Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

The following examples are provided to illustrate the present invention without, however, limiting the same thereto.

EXAMPLES

The following Examples are provided to illustrate certain aspects of the present invention and to aid those of skilled in the art in practicing this invention. These Examples are in no way to be considered to limit the scope of the invention in any manner.

Materials and Methods

Patients

In this study, twenty five children diagnosed with acute HSP in accordance with the criteria defined by the American College of Rheumatology (ACR) 1990 (Mills J A et al., Arthritis Rheum 1990 33:1114-1121) were enrolled at National Taiwan University Hospital (Taipei City, Taiwan) and twenty three healthy children with matching age and sex were also enrolled as controls. Serum samples were drawn from both groups, additionally; further serum samples from 15 patients (out of 25 patients) whom were in regression period were also collected.

Detection of Anti-Cardiolipin Antibodies

Briefly, 96-well high binding plates (Costar, Cambridge, Mass., USA) are coated with cardiolipin (CL) at 50 μg/ml in ethanol, air-dried. After incubating overnight at 4° C., plates are blocked with 10% bovine serum in phosphate-buffered saline (PBS, pH 7.4). Then, plasma samples (1:100 for IgG and IgM, 1:50 for IgA), and IgA fraction from patients (indicated concentrations) in 10% bovine serum/PBS were distributed into wells in duplicate and incubated for 1.5 hours at room temperature. A pooled normal human IgA (Jackson ImmunoResearch, West Grove, Pa., USA) was used as negative controls at the same concentrations. After washing with TBS, bound human IgG/A/M were detected by HRP-conjugated goat anti-human IgG/A/M (BioSource International, Camarillo, Calif., USA), and the peroxidase substrate tetramethylbenzidine (Kirkegaard & Perry Laboratories, Gaithersburg, Md., USA). Results were read at a wavelength of 450 nm against a background of 650 nm by use of a Thermomax plate reader (Molecular Devices Inc., Sunnyvale, Calif., USA).

Detection of Anti-Endothelial Cell Antibodies (AECA)

Human umbilical venous endothelial cells (HUVEC) were seeded on gelatin-coated 96-well microtiter plates (Nunc™, Demark) at a concentration of $1 \times 10^5$ cells/well. When cell growth reached confluent after 3-4 days, cells were fixed with 0.2% glutaraldehyde in PBS for 10 min at room temperature, and blocked with 1% bovine serum albumin (BSA)/PBS for 1 hour at 37° C. After washing with PBS, the plasma samples, diluted in 1% BSA/PBS at 1:100 for IgG/IgM detection; 1:50 for IgA detection, were incubated for 2 hours at 37° C. After washing with TBS, bound human IgG/A/M will be detected with HRP-conjugated goat anti-human IgG/A/M (BioSource International, Camarillo, Calif., USA), and the peroxidase substrate tetramethylbenzidine (Kirkegaard & Perry Laboratories, Gaithersburg, Md., USA). Results were read at a wavelength of 450 nm against a background of 650 nm with a Thermomax plate reader (Molecular Devices Inc., Sunnyvale, Calif., USA)

Detection of β2-GPI Antibodies

Briefly, 96-well high binding plates (Costar, Cambridge, Mass., USA) are coated with human β2GPI (Haematologic Technologies, Essex Junction, Vt., USA) or other unrelated proteins (prothrombin and OVA) at a concentration of 10 μg/ml in Tris-buffered saline (TBS, 0.05 M Tris-HCl and NaCl, PH 7.5). After incubating overnight at 4° C., plates are blocked with TBS containing 0.3% gelatin. Then, plasma samples (1:100 for IgG and IgM, 1:50 for IgA), and IgA fraction from patients (indicated concentrations) in TBS/0.1% gelatin are distributed into wells in duplicate and incubated for 1.5 hours at room temperature. A pooled normal human IgA (Jackson ImmunoResearch, West Grove, Pa., USA) were used as negative controls at the same concentrations. After washing with TBS, bound human IgG/A/M were detected with HRP-conjugated goat anti-human IgG/A/M (BioSource International, Camarillo, Calif., USA), and the peroxidase substrate tetramethylbenzidine (Kirkegaard & Perry Laboratories, Gaithersburg, Md., USA). Results were read at a wavelength of 450 nm against a background of 650 nm with a Thermomax plate reader (Molecular Devices Inc., Sunnyvale, Calif., USA)

Purification of IgA Antibodies

Circulating IgA immunoglobulins were isolated from 7 plasma samples positive for both CL and β2GPI by use of a commercial kit, Immobilized Jacalin (PIERCE, USA, USA), which isolates serum-circulating IgA1 by galactose-binding lectin.

Preparation of Synthetic β2GPI-Derived Peptides

In order to locate the binding epitopes of β-2-glycoprotein-1 to its autoantibodies, β-2-glycoprotein-1 was randomly divided into 15 fragments of peptides, which were prepared by use of an automatic solid-phase peptide synthesizer (ABI433A peptide synthesizer, Applied Biosystems Inc., Life Technologies Corp., Foster City, Calif., USA). Standard procedures of $N^\alpha$-9-fluorenylmethoxycarbonyl (Fmoc) chemistry were used to prepare these peptides. The primary sequence of each peptide is shown in TABLE 1.

All synthetic β2-GPI peptides were purified by reversed-phase high performance liquid chromatography (RP-HPLC) with a semi-preparative octadecyl ($C_{18}$) column. The mobile phase in the RP-HPLC is acetonitrile/water solvent system containing 0.1% trifluoroacetic acid (TFA). Detection was made at a wavelength of 220 nm and peaks were recorded and quantified. Eluate from each run of purification was collected and fractions with identical components were pooled together and then recovered by lyophilization in vacuum condition. The final purity of each collected peptide was determined by analytical RP-HPLC and 95% or higher in purity was achieved. For example, the purity of synthetic peptide, SEQ ID NO:11 was determined to be 95.23%. The synthetic peptides were kept frozen at −20° C. until used.

The purified β2-GPI synthetic peptides were further characterized for their molecular weights by electrospray ionization mass spectroscopy (ESI-MS). For example, molecular weight of synthetic peptide, SEQ ID NO:11 determined by ESI-MS was found to be 6244.4 daltons (calculated value=6247.2 daltons).

TABLE 1

The synthetic β2-GPI-derived peptides

| Peptide Number | Residue No. in β2-GPI | Amino Acid Sequence | SEQ ID No |
|---|---|---|---|
| 1 | 1-28 | H₂N-MISPVLILFSSFLCHVAIAGRTCP KPDD-COOH | 1 |
| 2 | 21-52 | H₂N-RTCPKPDDLPFSTVVPLKTFYE PGEEITYSCK-COOH | 2 |

TABLE 1-continued

The synthetic β2-GPI-derived peptides

| Peptide Number | Residue No. in β2-GPI | Amino Acid Sequence | SEQ ID No |
|---|---|---|---|
| 3 | 52-78 | H₂N-KPGYVSRGGMRKFICPLTGLWPINTLK-COOH | 3 |
| 4 | 78-96 | H₂N-KCTPRVCPFAGILENGAVR-COOH | 4 |
| 5 | 96-123 | H₂N-RYTTFEYPNTISFSCNTGFYLNGADSAK-COOH | 5 |
| 6 | 120-139 | H₂N-DSAKCTEEGKWSPELPVCAP-COOH | 6 |
| 7 | 129-157 | H₂N-KWSPELPVCAPIICPPPSIPTFATLRVYK-COOH | 7 |
| 8 | 154-184 | H₂N-RVYKPSAGNNSLYRDTAVFECLPQHAMFGND-COOH | 8 |
| 9 | 184-212 | H₂N-DTITCTTHGNWTKLPECREVKCPFPSRPD-COOH | 9 |
| 10 | 210-228 | H₂N-RPDNGFVNYPAKPTLYYKD-COOH | 10 |
| 11 | 229-285 | H₂N-KATFGCHDGYSLDGPEEIECTKLGNWSAMPSCKASCKVPVKKATVVYQGERVKIQEK-COOH | 11 |
| 12 | 286-305 | H₂N-FKNGMLHGDKVSFFCKNKEK-COOH | 12 |
| 13 | 303-320 | H₂N-KEKKCSYTEDAQCIDGTI-COOH | 13 |
| 14 | 317-336 | H₂N-DGTIEVPKCFKEHSSLAFWK-COOH | 14 |
| 15 | 327-345 | H₂N-KEHSSLAFWKTDASDVKPC-COOH | 15 |

Detection of IgA Anti-β2-GPI-Derived Peptides Antibodies

Briefly, 96-well high binding plates (Costar, Cambridge, Mass., USA) are coated with human β-2-GPI peptides 1-15 at a concentration of 10 (g/ml in Tris-buffered saline (TBS, 0.05 M Tris-HCl and NaCl, PH 7.5). After incubating overnight at 4° C., plates are blocked with TBS containing 0.3% gelatin. Then, plasma samples (1:50 for IgA), and IgA fraction from patients (indicated concentrations) in TBS/0.1% gelatin were distributed into wells in duplicate and incubated for 1.5 hours at room temperature. A pooled normal human IgA (Jackson ImmunoResearch, West Grove, Pa., USA) will be used as negative controls at the same concentrations. After washing with TBS, bound human IgG/A/M were detected with HRP-conjugated goat anti-human IgA (BioSource International, Camarillo, Calif., USA), and the peroxidase substrate tetramethylbenzidine (Kirkegaard & Perry Laboratories, Gaithersburg, Md., USA). Results were read at a wavelength of 450 nm against a background of 650 nm with a Thermomax plate reader (Molecular Devices Inc., Sunnyvale, Calif., USA).

Results

β2-GPI is an Antigen for the Occurrence of Acute HSP

Figure 2:
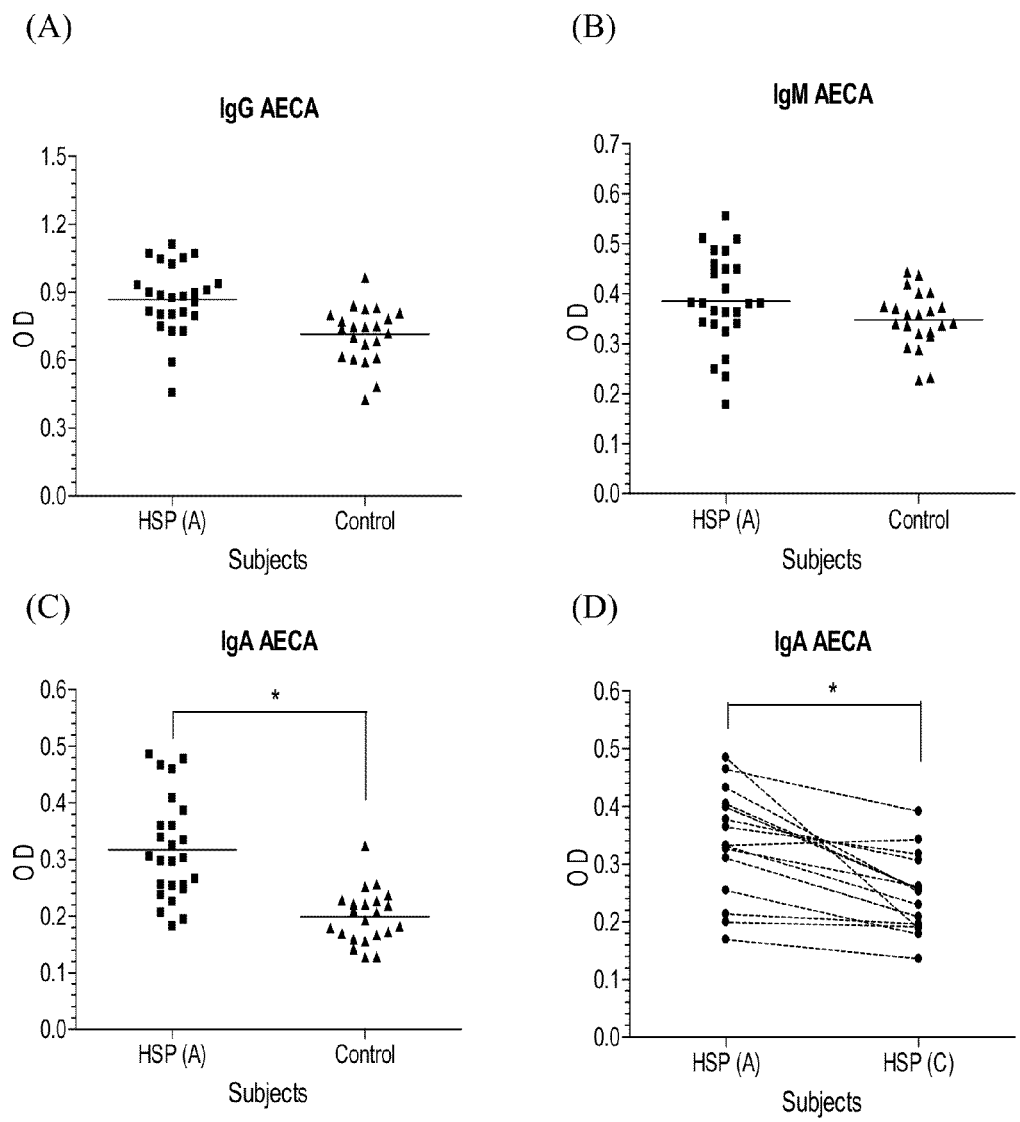
FIG. 2A to 2C illustrate the plasma levels of (A) IgG, (B) IgM, (C) IgA against endothelial cell (presented as OD) measured in children with acute HSP in accordance with one embodiment of this invention, a mean value in each group is represented by a lateral line in each panel.
FIG. 2D is a comparison of IgA anti-endothelial cell antibody (AECA) level between patients with acute HSP (A) and HSP patients whom are in convalescent phase (C), dashed lines illustrate the data points that are in comparison, with * indicates those that are statistically significant.
Figure 3:
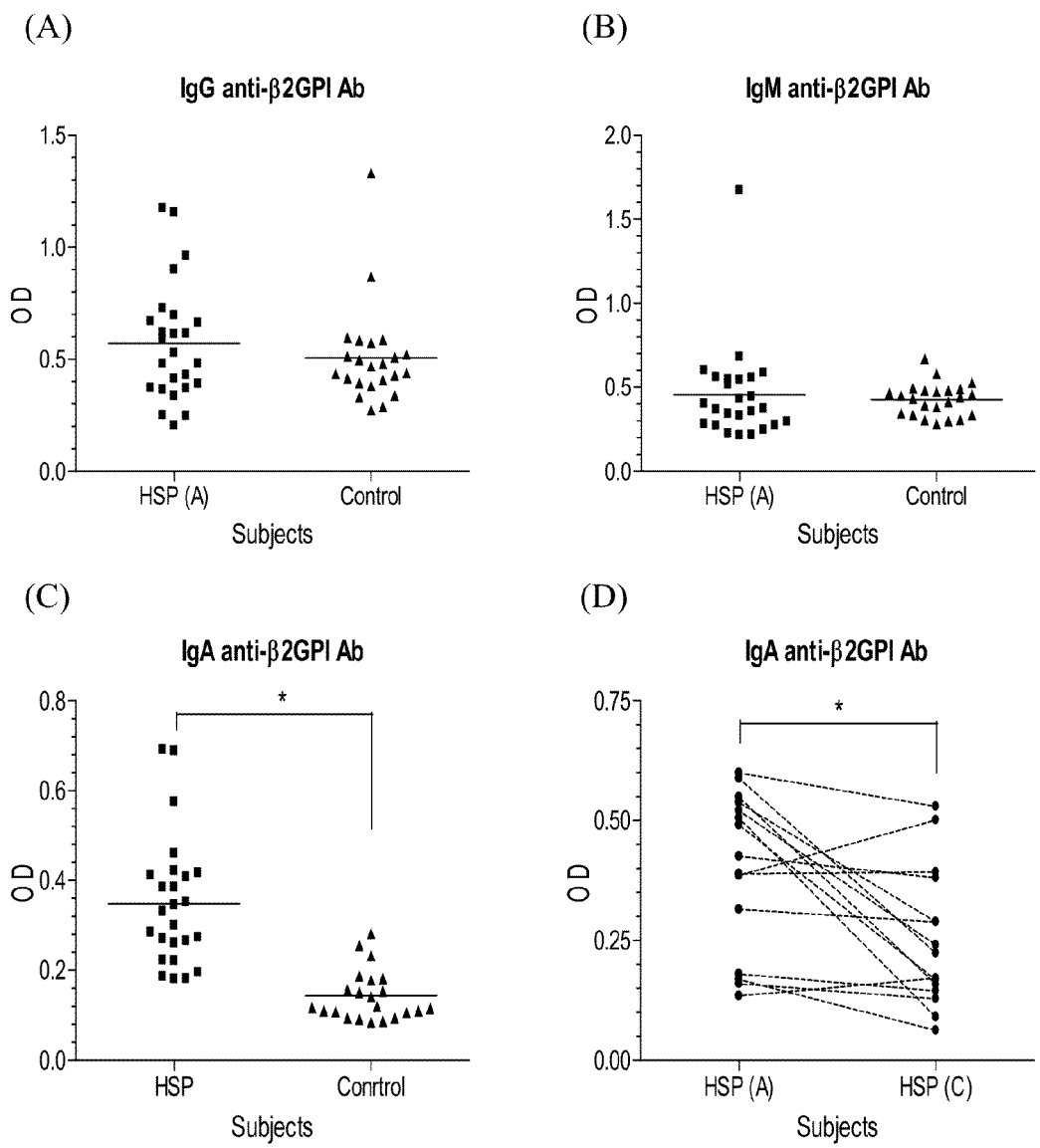
FIG. 3A to 3C illustrates the plasma levels of (A) IgG, (B) IgM, (C) IgA against β2-GPI (presented as OD) measured in children with acute HSP in accordance with one embodiment of this invention, a mean value in each group is represented by a lateral line in each panel.
FIG. 3D is a comparison of IgA anti-β2-GPI antibody level between patients with acute HSP (A) and HSP patients whom are in convalescent phase (C), dashed lines illustrate the data points that are in comparison, with * indicates those that are statistically significant.
Figure 4:
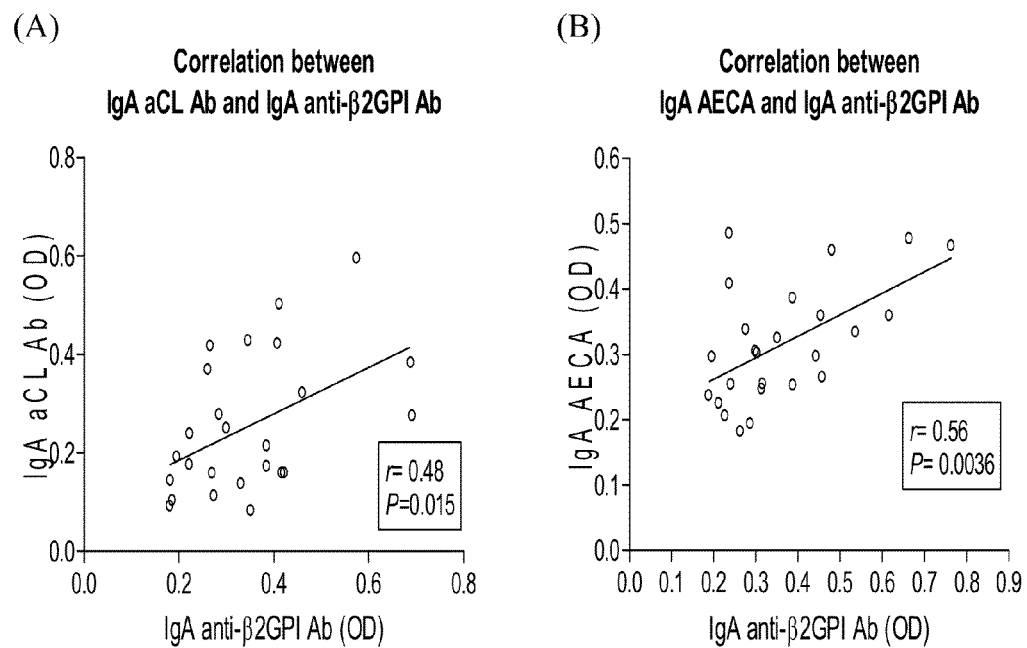
FIG. 4A illustrates the correlation between IgA aCL antibodies and IgA anti-β2-GPI antibodies in children with acute HSP in accordance with one embodiment of this invention.
FIG. 4B illustrates the correlation between IgA AECA and IgA anti-β2-GPI antibodies in children with acute HSP in accordance with one embodiment of this invention.

Inventors of this study identified that patients diagnosed with acute HSP exhibited significantly higher amounts of IgA anti-cardiolipin (aCL) (FIG. 1), IgA anti-endothelial cell (IgA AECA) (FIG. 2), and IgA anti-β2-GPI antibodies (FIG. 3) than those of healthy individuals; and positive correlation between IgA anti-β2-GPI antibodies and IgA aCL or IgA AECA were also found (FIG. 4), which suggested that β2-GPI may be an antigen for HSP occurrence, and therefore a useful biomarker for detecting and diagnosing patients with HSP.

Figure 5:
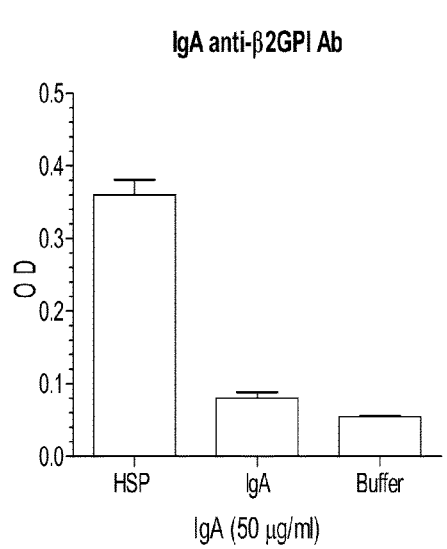
FIGS. 5A and 5B illustrate the reactivity of polyclonal IgA (i.e., IgA group, 50 (g/ml) and IgA purified from seven chosen patients' plasma samples (i.e., HSP group, 50 (g/ml) with either antigen (A) β2-GPI or (B) aCL in accordance with one embodiment of this invention.
FIGS. 5C and 5D illustrate the dose dependency of polyclonal IgA or IgA isolated from two chosen patient samples (IgA1 and IgA2) with antigen (C) β2-GPI or (D) aCL in accordance with one embodiment of this invention.
Figure 5:
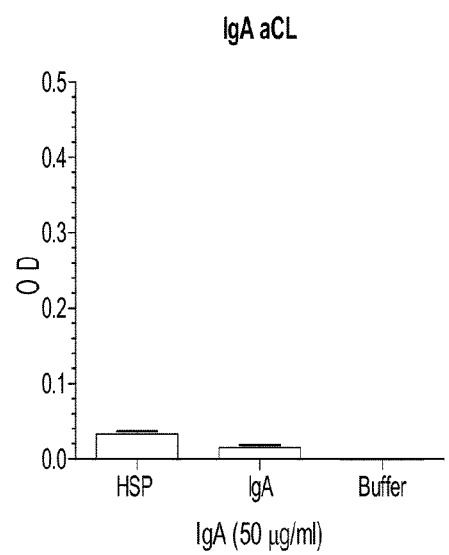
Figure 5:
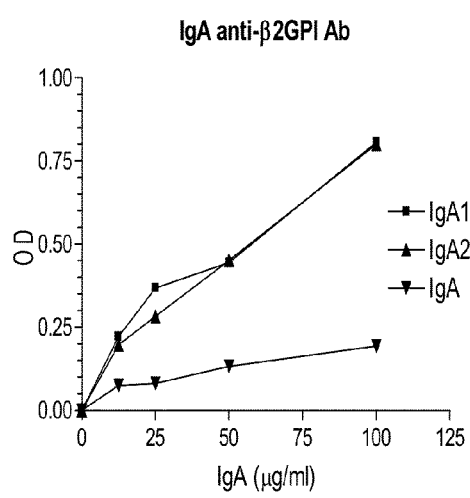
Figure 5:
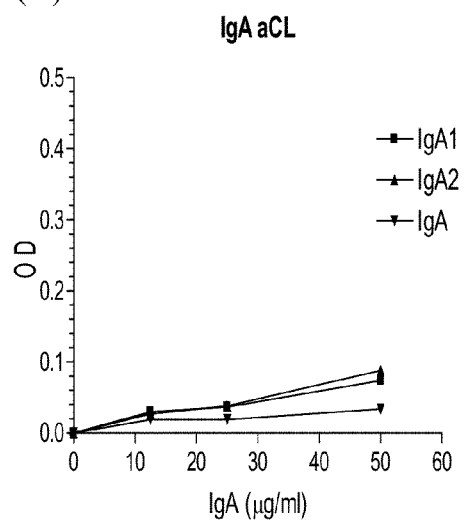
Figure 6:
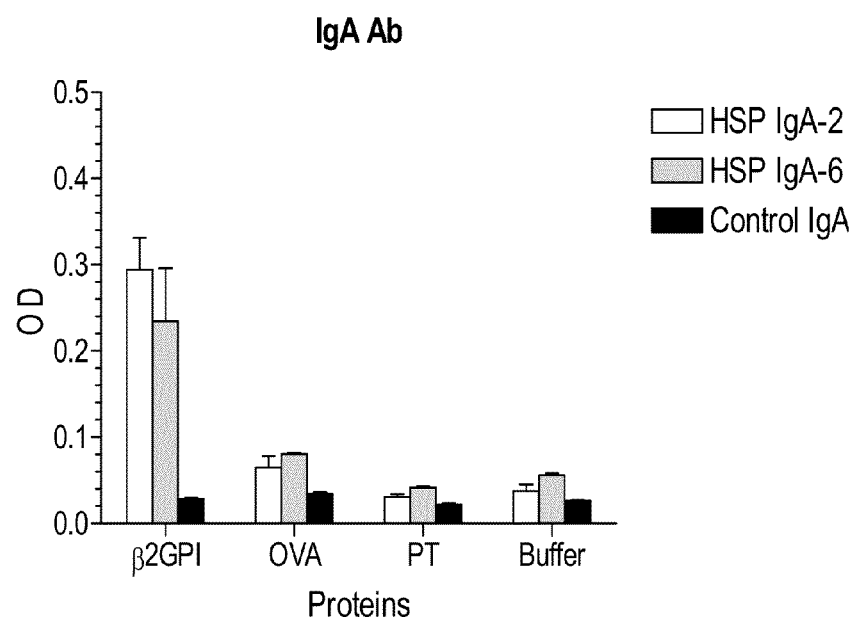
FIG. 6 illustrates the binding specificity of the autoantibody IgA isolated from two randomly chosen samples (IgA2, IgA6 at 10 (g/ml) with various proteins including β2-GPI, ova albumin (OVA) and prothrombin (PT) in accordance with one embodiment of this invention.

To substantiate whether β2-GPI is a useful antigen or biomarker for detecting the occurrence of acute HSP among children, total IgA form 7 patients who exhibited high concentrations of both IgA anti-cardiolipin antibodies and IgA anti-β2-GPI antibodies were collected, and subjected to purification to remove other serum proteins completely. It was found that the purified IgA antibodies would bind to β2-GPI, instead of cardiolipin (FIGS. 5A and 5B). Analysis from two serum samples of HSP patients (hereafter IgA1 and IgA2) further showed that the binding between IgA and β2-GPI were in dose-dependent manner (FIGS. 5C and 5D), the amount of bound IgA anti-β2-GPI antibody complex increased with an increase in IgA concentration. A negative control using two other un-related proteins, oval albumin (OVA) and prothrombin, confirmed that the binding between IgA autoantibodies and β2GPI is specific. Specifically, the same serum samples as described above (hereafter IgA2 and IgA6) were mixed and reacted with OVA and prothrombin, respectively, and the binding of IgA autoantibodies with either OVA or prothrombin is negligible (FIG. 6).

β2-GPI-Derived Peptides are Useful Antigens or Biomarkers for Detecting or Diagnosing HSP To locate the binding epitopes of β2-GPI, β2-GPI was randomly cut into 15 smaller fragments of peptides and synthesized accordingly by the procedures described above. The synthetic peptides were designated as P1 to P15, each with an amino acid sequence as set forth in SEQ ID NO: 1 to 15, respectively.

Figure 7:
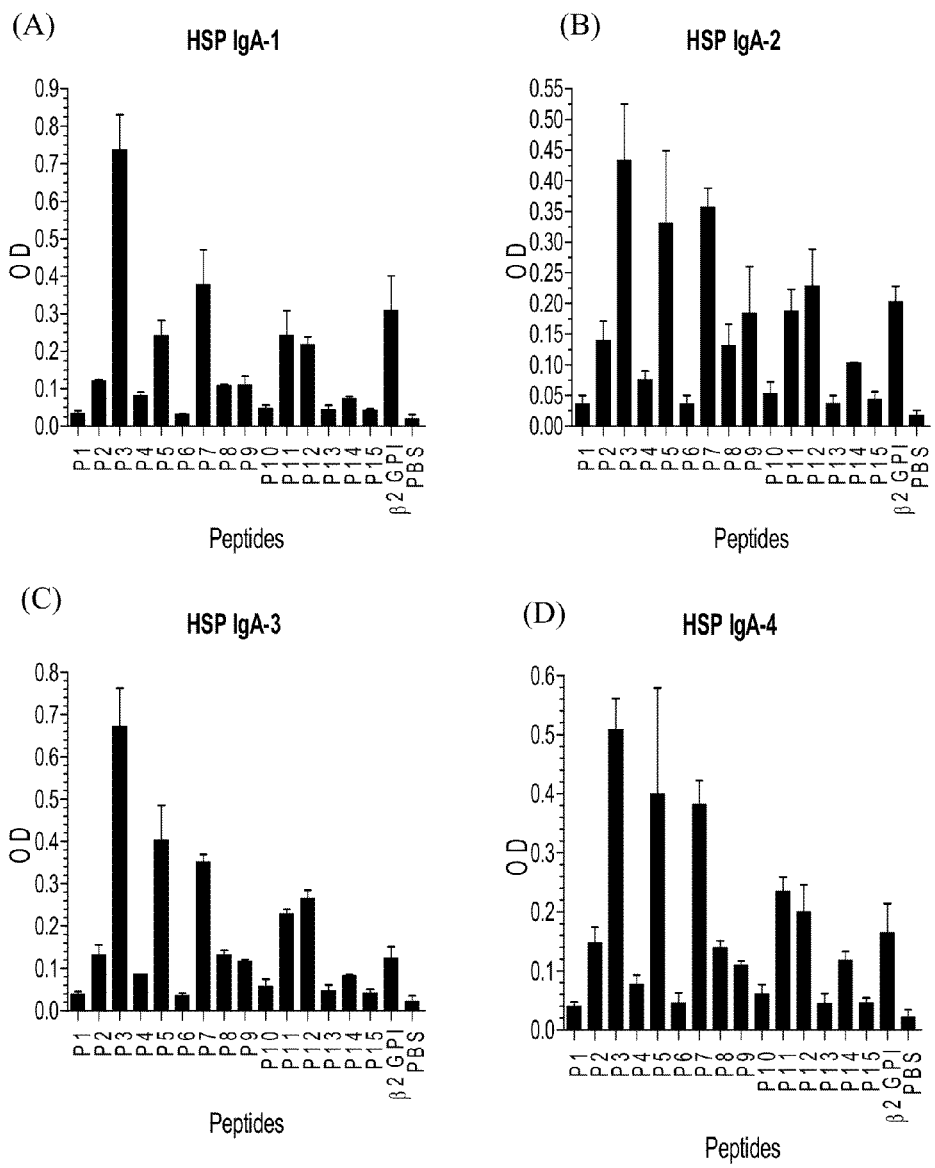
FIG. 7A to 7H illustrate the reactivity of 7 IgA samples (i.e., IgA1-7 at 10 (g/ml) with 15 synthetic peptides of β2-GPI (i.e., P-1 to P-15) in accordance with one embodiment of this invention; the binding of IgA with β2-GPI (expressed as OD) was used as a positive control, and the binding with a buffer solution (PBS) was used as a negative control. OD values that were higher than that of the positive control are regarded as significant bindings.
Figure 7:
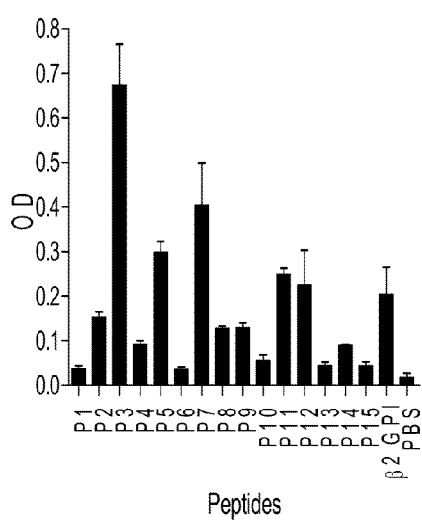
Figure 7:
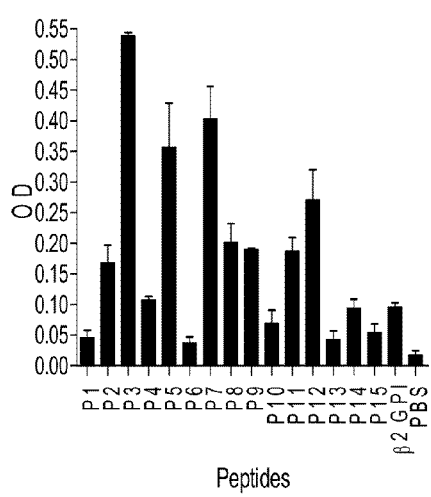
Figure 7:
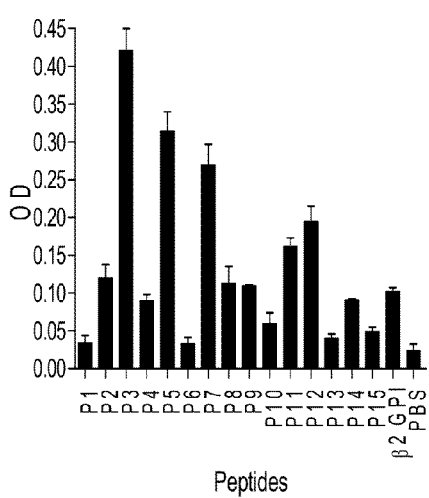
Figure 7:
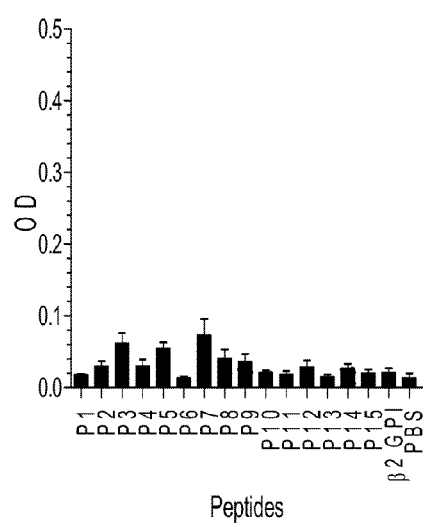
Figure 8:
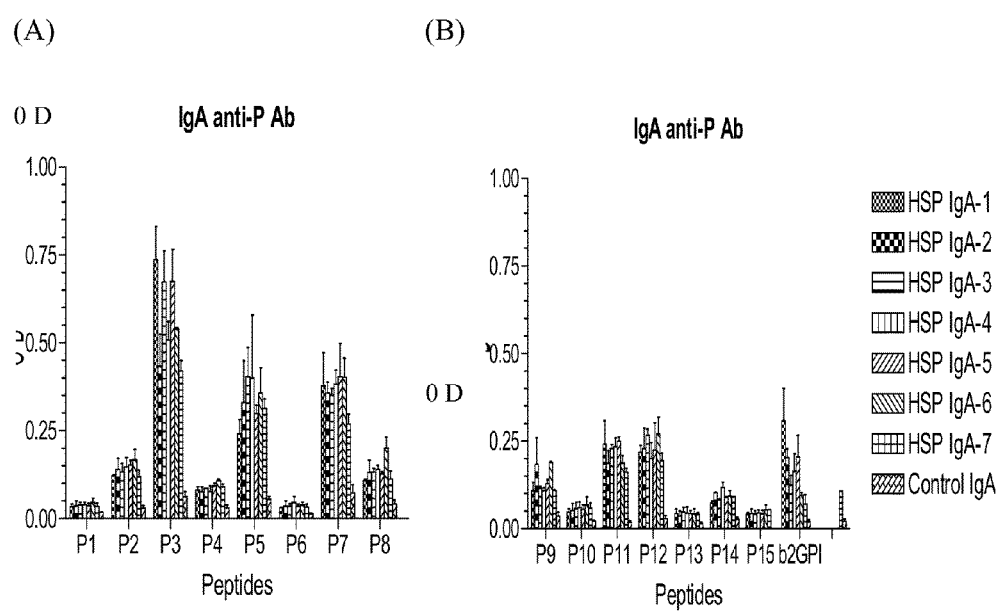
FIG. 8 illustrates a summarized result of FIG. 7, in which significant binding were found between IgA, which were derived from 7 patients with acute HSP (n=7), and any of the synthetic peptide 3, 5 or 7 (FIG. 8A) and synthetic peptide 11 or 12 (FIG. 8B)
Figure 9:
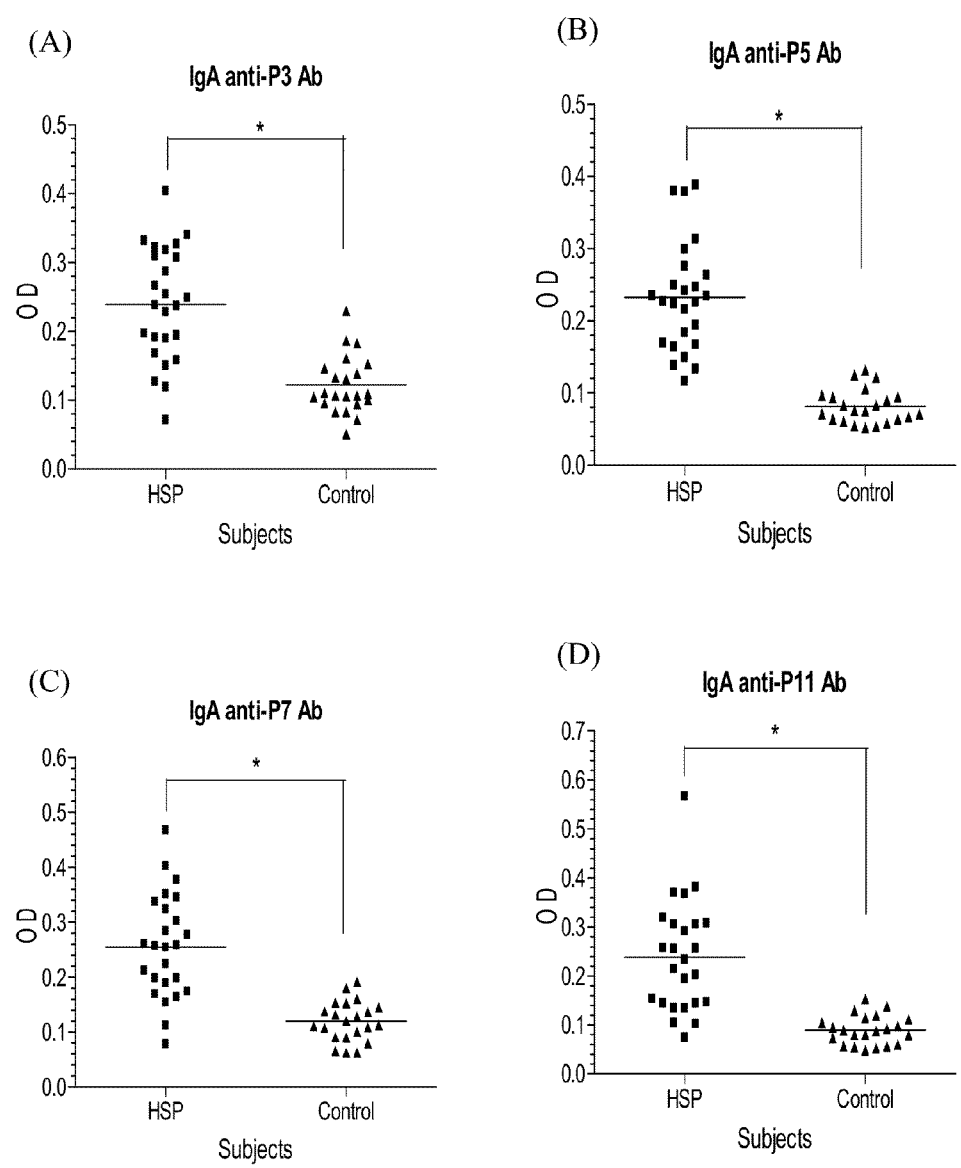
FIG. 9 illustrate the plasma level of IgA autoantibodies against synthetic peptide 3, 5, 7, 11, 12 and 6 (i.e., P3, P5, P7, P11, P12 and P6), respectively in children with acute HSP.
Figure 9:
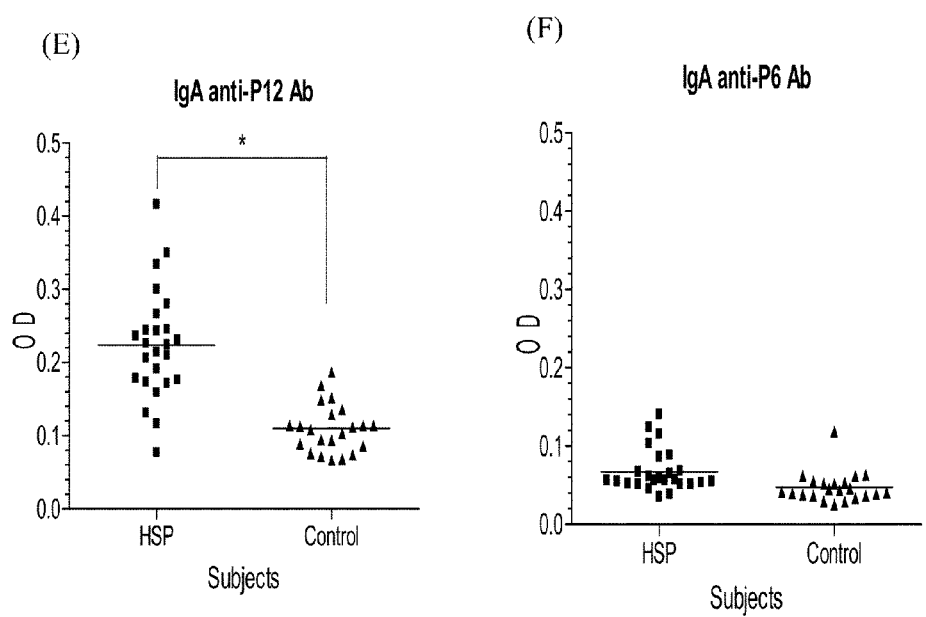

Binding assay performed in accordance with the procedures described above indicated that plasma level of IgA anti-β2-GPI peptides (including P3, P5, P7, P11 and P12, each with an amino acid sequence as set forth in SEQ ID NO: 3, 5, 7, 11 and 12, respectively) antibodies in children with acute HSP were significantly higher than those in healthy subjects (expressed as OD, p<0.0001), in which the binding strength is most significant for synthetic peptide P3 (FIGS. 7, 8 and 9).

INDUSTRIAL APPLICABILITY

The present invention provides a novel and rapid solution for early detecting or diagnosing patients with HSP by use of specific antigens or biomarkers, e.g., β2-GPI-derived peptides. The synthetic peptides, methods and kits according to the present invention allows physicians to easily detect or diagnose HSP patients by relying on objective means or markers (i.e., β2-GPI-derived peptides), instead of subjective means such as history, or judgments made by a physician based on his experience or the development of symptoms in such patients.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A synthetic peptide capable of forming a complex with an IgA autoantibody in a biological sample of a subject having or suspected of having Henoch-Schönlein purpura in an immunological assay, wherein the synthetic peptide consists of SEQ ID NO: 11.

2. A method for detecting or diagnosing Henöch-Schönlein purpura (HSP) in a subject having or suspected of having HSP, comprising:
   obtaining a biological sample from the subject;
   mixing the biological sample with the synthetic peptide of claim 1, so as to react IgA autoantibody to β-2-glycoprotein-1 in the biological sample with the synthetic peptide of claim 1 and thereby form a complex;
   measuring the complex in an immunological assay, thereby measuring IgA autoantibody to β-2-glycoprotein-1 in the biological sample;
   comparing the amount of IgA autoantibody to β-2-glycoprotein-1 in the biological sample with that of a control from a healthy individual; and
   detecting or diagnosing HSP in the subject when the amount of IgA autoantibody to β-2-glycoprotein-1 in the biological sample is higher than that of the control.

3. The method of claim 2, wherein the immunological assay is an ELISA.

4. The method of claim 2, wherein the biological sample is selected from the group consisting of a whole blood sample, a plasma sample, a serum sample, and purified or filtered forms thereof.

5. A kit for detecting or diagnosing HSP in a subject having or suspected of having HSP, comprising:
- a container;
- the synthetic peptide of claim 1; and
- a legend associated with the container indicating how to use the synthetic peptide to detect an IgA autoantibody in a biological sample of the subject.

6. The kit of claim 5, further comprising at least one additional synthetic peptide selected from the group consisting of SEQ ID NO: 3, SEQ ID NO: 5, SEQ ID NO: 7, and SEQ ID NO: 12.

7. The kit of claim 6, wherein the at least one additional synthetic peptide consists of SEQ ID NO: 3.

\* \* \* \* \*